(12) United States Patent
Crofts et al.

(10) Patent No.: US 11,557,397 B2
(45) Date of Patent: Jan. 17, 2023

(54) METHOD OF CONTROLLING A GARMENT TO RECORD ACTIVITY DATA

(71) Applicant: Prevayl Innovations Limited, Manchester (GB)

(72) Inventors: Adam Lee Edward Crofts, Manchester (GB); Tahir Mahmood, Manchester (GB)

(73) Assignee: Prevayl Innovations Limited, Manchester (GB)

( * ) Notice: Subject to any disclaimer, the term of this patent is extended or adjusted under 35 U.S.C. 154(b) by 0 days.

(21) Appl. No.: 17/432,586

(22) PCT Filed: Jun. 5, 2020

(86) PCT No.: PCT/GB2020/051361
§ 371 (c)(1),
(2) Date: Aug. 20, 2021

(87) PCT Pub. No.: WO2020/245596
PCT Pub. Date: Dec. 10, 2020

(65) Prior Publication Data
US 2022/0101994 A1   Mar. 31, 2022

(30) Foreign Application Priority Data
Jun. 7, 2019 (GB) .................... 1908187

(51) Int. Cl.
*G16H 40/67* (2018.01)
*G16H 20/30* (2018.01)
*H04L 9/40* (2022.01)

(52) U.S. Cl.
CPC ............. *G16H 40/67* (2018.01); *G16H 20/30* (2018.01); *H04L 63/08* (2013.01)

(58) Field of Classification Search
CPC ......... G16H 40/67; G16H 20/30; H04L 63/08
See application file for complete search history.

(56) References Cited

U.S. PATENT DOCUMENTS

| | | | |
|---|---|---|---|
| 2011/0062237 A1* | 3/2011 | Chaves | G06K 19/06056 29/829 |
| 2014/0318699 A1 | 10/2014 | Longinotti-Buitoni et al. | |
| 2015/0081169 A1* | 3/2015 | Pisz | H04W 4/40 701/1 |

(Continued)

FOREIGN PATENT DOCUMENTS

KR    101907383    10/2018

OTHER PUBLICATIONS

Naked Labs (https://nakedlabs.com/naked-home-body-scanner, available at least from Oct. 4, 2018, 2 pages) (Year: 2018).*

(Continued)

*Primary Examiner* — Oleg Korsak
(74) *Attorney, Agent, or Firm* — Haley Guiliano LLP (57) ABSTRACT

The method comprises receiving a representation of a visual symbol, wherein the visual symbol comprises a code string identifying the garment that is encoded into the visual symbol (101). The method comprises establishing, based on the representation of the visual symbol, the identity of the garment (102). The method comprises transmitting, to the identified garment, an authorisation code to activate a sensor of the garment to record activity data (103).

8 Claims, 7 Drawing Sheets

(56) References Cited

U.S. PATENT DOCUMENTS

| | | |
|---|---|---|
| 2017/0243615 A1 | 8/2017 | Tabak |
| 2018/0174683 A1 | 6/2018 | Franz et al. |
| 2018/0345079 A1 | 12/2018 | Lindman et al. |
| 2019/0037932 A1 | 2/2019 | Martin et al. |
| 2019/0246734 A1* | 8/2019 | Nurse .................. A61B 5/6807 |

OTHER PUBLICATIONS

GB Combined Search Report and Examination Report dated Dec. 12, 2019 of GB Application 1908187.6.
GB $2^{nd}$ Examination Report dated May 29, 2020 of GB Application 1908187.6.
International Search Report and Written Opinion of PCT/GB2020/051361 dated Aug. 4, 2020.
Peter Lightbody et al.: "A versatile high-performance visual fiducial marker detection system with scalable identity encoding", Applied Computing, ACM, 2 Penn Plaza, Suite 701 New York NY 10121-0701 USA, Apr. 3, 2017 pp. 276-282, XP058337320.
"Enflux exercise clothing", kickstarter.com, [online] available from https://www.kickstarter.com/projects/1850884998/enflux-smart-clothing-3d-workout-tracking-and-form/description.
"EMGlare Heart" emglare.com, [online] available from https://emglare.com/.
YouTube Video, titled "QR Code & Bluetooth Connection Tutorial with Shimmer", purportedly uploaded by "Shimmer Sensing" on Feb. 6, 2014, available from https://www.youtube.com/watch?v=I6p ZLr2h9ag Screenshot provided (taken on Aug. 13, 2021).

* cited by examiner

METHOD OF CONTROLLING A GARMENT TO RECORD ACTIVITY DATA

CROSS-REFERENCE TO RELATED APPLICATIONS

This application is a national stage application under 35 U.S.C. § 371 of International Application PCT/GB2020/051361, filed Jun. 5, 2020, which claims priority of GB Patent Application 1908187.6 filed Jun. 7, 2019. The disclosure of which are hereby incorporated by reference herein in their entireties.

BACKGROUND

The present invention is directed towards a method, garment and system. The present invention is directed in particular towards controlling a sensor incorporated into the garment to record activity data.

Garments incorporating sensors are wearable electronics designed to interface with a wearer of the garment, and to determine information such as the wearer's heart rate, rate of respiration, activity level, and body positioning. Such properties can be measured via skin contact with a sensor assembly that includes a sensor for signal transduction and/or microprocessors for analysis. Such garments are commonly referred to as 'smart clothing'.

It would be desirable to provide a mechanism for controlling a sensor incorporated into the garment to record activity data.

SUMMARY

According to the present disclosure there is provided a method, garment and system as set forth in the appended claims. Other features of the invention will be apparent from the dependent claims, and the description which follows.

According to a first aspect of the invention, there is provided method. The method comprises receiving a representation of a visual symbol of a garment. The visual symbol comprises a code string identifying the garment that is encoded into the visual symbol. The method comprises establishing, based on the representation of the visual symbol, the identity of the garment. The method comprises transmitting, to the identified garment, an authorisation code to activate a sensor of the garment to record activity data.

Significantly, a garment comprising a marker is provided. The marker comprises a (unique) code string identifying the garment encoded into a visual symbol. When the visual symbol is imaged and the data string is obtained from the image, the data string is used to activate a sensor of the garment to record activity data. In this way, the sensor of the garment may be controlled to record activity data via the process of imaging the garment and processing the resultant image.

The method therefore enables the sensor of the garment to be controlled using a simple electronic device such as a portable electronic device with an integrated camera Beneficially, the sensor of the garment is controlled through a simple and intuitive procedure of imaging the garment. This approach enables a user to control when the sensor of the garment records activity data. This may be beneficial in reducing the power consumption of the garment such that the sensor is only activated to record activity data at user desired times. The visual symbol may be located on an outside surface or otherwise readable from the outside surface of the garment so that it may easily be read by the electronic device.

The representation of the visual symbol may be a data string representing the visual symbol.

Establishing, based on the data string, the identity of the garment may comprise decoding the data string so as to obtain the code string and may further comprise identifying the garment based on the code string. The data string may be a simple digitised representation of the visual symbol or may be an encrypted version of the code string. The method may run a decoding algorithm to generate the code string from the data string.

A database may be provided which may store one or a plurality of code strings each associated with a different garment. The identity of the garment may be established based on which of the code strings in the database the generated data string (once decoded) matches.

The method may further comprise obtaining a user credential from a user. The sensor may only be activated to record activity data if the user is authorised, based on the obtained user credential, as having permission to access the activity data.

The method may further comprise receiving a user credential. The method may further comprise establishing, based on the user credential, whether the user is authorised to activate the sensor. The method may further comprise transmitting the authorisation code to the identified garment only if the user is authorised to activate the sensor.

The user credential may be in the form of a password or passcode. The user credential may be in the form of biometric data. Different users may have different permissions levels and thus may have permission to access different sensors on the garment or to access different recording operations performed by the sensor. For example, a sensor may be able to record a plurality of different types of biodata, but a user may only have permission to activate the sensor to record one or a subset of those types of biodata. The method may comprise determining, from the user credential, the permission level of the user, and may comprise activating the sensor based on the determined permission level.

Receiving the representation of the visual symbol may comprise: obtaining an image of the garment; and processing the image to generate the representation of the visual symbol.

The visual symbol may be part of a fiducial marker of the garment. The fiducial marker may be located on the outside surface of the garment or may be otherwise readable from the outside surface of the garment. The method may further comprise processing the image to determine the location of the fiducial marker.

Beneficially, a fiducial marker is useable as a point of reference for the garment and thus enables the position of the garment and the motion of the garment over time to be monitored simply by capturing images of the garment. In this way, a single marker on the garment is not only used to identify the garment but also beneficially allows for the motion of the garment to be monitored. The fiducial marker may be in the form of a 2D image. The fiducial marker of the present invention is beneficial as it is simple, of low cost and does not negatively affect the comfort of the garment for the wearer. The fiducial marker may be an augmented reality (AR) marker with additional information in the form of the code string encoded therein.

The fiducial marker may have a limited visual footprint on the garment. This means that the fiducial marker may be sufficiently small that it is not easily visible by the naked eye but is still visible in the captured image. In this way, the fiducial marker does not affect or has a minimal effect on the appearance of the garment. In some examples, the fiducial marker is visible to the naked eye.

The method may further comprise receiving the recorded activity data from the garment.

The method may further comprise displaying a representation of the received activity data on a display.

The method may further comprise simultaneously displaying a representation of a wearer of the garment with the representation of the activity data on the display.

The position of the representation of the activity data on the display may be determined according to the determined location of the fiducial marker.

The position of the representation of the activity data may be determined by applying a predetermined displacement to the coordinate location of the fiducial marker.

The position of the representation of the activity data may correspond to the position of a feature of interest on a wearer of the garment.

The method may further comprise simultaneously displaying a representation of a wearer of the garment with the representation of the activity data on the display.

The representation of the activity data may at least partially overlay the displayed representation of the wearer. Beneficially, the display of the activity data is enhanced by positioning the activity data over the representation of the wearer so that the user can understand the relationship between the activity data and a relevant physiological component of the wearer.

Displaying the representation of the wearer of the garment may comprise displaying the obtained image. The obtained image may be a live view image. That is, a real-time video otherwise known as a live video feed. That is the camera may capture live view image data which may then be displayed on the display of the apparatus performing the method. The user may therefore view a live view image of the wearer.

Displaying the representation of the wearer of the garment may comprise displaying an avatar representation of the wearer, optionally wherein the avatar representation of the wearer is a 3D representation of the wearer. The avatar may be animated to mimic the motion of the wearer. The avatar may be animated based on motion data obtained from one or more motion sensors of the garment.

The representation of the activity data may be in the form of an augmented reality object.

The representation of the activity data may represent a physiological state of the wearer. The physiological state may relate to a muscle or muscle group of the wearer, an organ of the wearer such as the heart or lung(s), or a condition such as the wearer's hydration level.

The activity data may comprise activity data related to a muscle or muscle group of a wearer of the garment. The position of the representation of the activity data may be determined to correspond to an estimated location of the muscle or muscle group of the wearer as determined from the location of the fiducial marker. The method may comprise simultaneously displaying a representation of the wearer with the representation of the activity data. The representation of the activity data may be displayed such that it overlays the representation of the wearer at the position corresponding to the estimated location of the muscle or muscle group of the wearer.

The muscle or muscle groups may comprise one or more of the triceps, deltoids, pectorals, abdominals, quadriceps, hamstrings, gluteals, and forearms.

The representation of the activity data may represent a physiological state of the muscle or muscle group such as whether the muscle or muscle group are in contraction or relaxation. The representation of the activity data may convey information relating to the activity level of the muscle or muscle group such that the representation may have a darker or lighter colour depending on the intensity of the activity performed by the user.

The activity data may comprise cardiac activity data. The position of the representation of the activity data may be determined to correspond to an estimated location of the heart of a wearer of the garment as determined from the location of the fiducial marker. The method may comprise simultaneously displaying a representation of the wearer with the representation of the activity data. The representation of the activity data may be displayed such that it overlays the representation of the wearer at the position corresponding to the estimated location of the heart of the wearer.

The representation of the activity data may represent a physiological state of the heart such as the heart rate.

The representation of the activity data may be in the form of an augmented reality object.

The representation of the activity data may be in the form of a 2D or 3D object of a feature of interest of the wearer such as a muscle, muscle group or organ. The object may be in the form of a 2D or 3D model of a heart. The model of the heart may be animated to beat at a rate corresponding to the heart rate of the wearer as determined from the activity data.

The obtained image may be captured by a camera. The camera may capture a live view image. Obtaining the image may therefore comprise capturing the image by a camera. The camera may be part of an apparatus performing the method or may be communicatively coupled to the apparatus.

The method may be performed by a server or other electronic apparatus such as a user electronic device. In some examples, the method is performed by a server in communication with a user electronic device. As a result, an electronic device which may not be in direct communication with the garment is able to control the recording of activity data by the sensor.

According to a second aspect of the invention, there is provided an apparatus arranged to perform the method of the first aspect of the invention. The apparatus may be a user electronic device or a server.

According to a third aspect of the invention, there is provided a garment. The garment comprises a sensor. The garment comprises a communication unit. The garment comprises at least one marker, the at least one marker comprising a code string identifying the garment encoded into a visual symbol. The communication unit is arranged to receive an authorisation code, the authorisation code being generated according to the at least one marker. The sensor is arranged to be activated to record activity data according to the authorisation code received by the communication unit.

The communication unit may be arranged to receive activity data for the wearer from the sensor and transmit the activity data to an external device. The at least one marker may be a fiducial marker.

The sensor may be able to record a plurality of different types of activity data. The sensor may be arranged to be activated to record all or a subset of the types of activity data according to the received authorisation code.

The garment may comprise a plurality of sensors, and one or more of the sensors are activated according to the authorisation code received by the communication unit.

The at least one marker may be located on an outside surface of the garment.

The garment may be suitable for the method of the first aspect of the invention.

The marker may be a 2D image. The marker may be a fiducial marker optionally in the form of a 2D image. The marker may be an Augmented Reality (AR) marker with additional information in the form of the code string encoded therein.

The marker may comprise a plurality of markers. The plurality of markers may be located at different locations on the garment. The plurality of markers may be arranged in a geometric pattern. The plurality of markers may be arranged together on the garment to form a decorative item.

The plurality of markers may be located at different locations on the garment.

The marker may be integrated into the garment.

The marker may be printed onto the garment. Any known garment printing technique may be used such as screen printing or inkjet printing. The marker may be incorporated onto the garment using a direct to garment printing technique.

The marker may be incorporated into the stitching of the garment, and/or a seam of the garment, and/or a hem of the garment, and/or a neckline of the garment, and/or a collar of the garment, and/or a sleeve of the garment, and/or a cuff of the garment, and/or a pocket of the garment, and/or a body of the garment, and/or a fastener of the garment. The fastener may be a zipper, button, clasp, toggle, stud, snap fastener, popper, eyelet, buckle, tie or ribbon.

The sensor may comprise a plurality of sensors.

The sensor may be arranged to sense one or more signals external to the wearer. The sensor may be any or a combination of a temperature sensor, a camera, a location tracking module such as a GPS module, and a chemical sensor.

The sensor may be a biosensor arranged to measure one or more biosignals of a user wearing the wearable article. Here, "biosignal" may refer to any signal in a living being that can be measured and monitored. The term "biosignal" is not limited to electrical signals and can refer to other forms of non-electrical biosignals. The biosensor may be used for measuring one or a combination of bioelectrical, bioimpedance, biochemical, biomechanical, bioacoustics, biooptical or biothermal signals of the wearer. The bioelectrical measurements include electrocardiograms (ECG), electrogastrograms (EGG), electroencephalograms (EEG), and electromyography (EMG). The bioimpedance measurements include plethysmography (e.g., for respiration), body composition (e.g., hydration, fat, etc.), and electroimpedance tomography (EIT). The biomagnetic measurements include magnetoneurograms (MNG), magnetoencephalography (MEG), magnetogastrogram (MGG), magnetocardiogram (MCG). The biochemical measurements include glucose/lactose measurements which may be performed using chemical analysis of the wearer's sweat. The biomechanical measurements include blood pressure. The bioacoustics measurements include phonocardiograms (PCG). The biooptical measurements include orthopantomogram (OPG). The biothermal measurements include skin temperature and core body temperature measurements. The biosensor may comprise a radar unit. The garment may sense a combination of external signals and biosignals of the wearer.

In some examples, the marker has a limited visual footprint on the garment. This means that the marker is sufficiently small that it is not easily visible by the naked eye but is still visible in the image captured by the image capturing device. In this way, the marker does not affect or has a minimal effect on the appearance of the garment. In some examples, the marker is visible to the naked eye.

The marker may be incorporated into or form part of visual element on the garment which may be a decorative item in the garment. The decorative item may be a logo, design, image or pattern on the garment. In this way, the marker may contribute to or enhance the appearance of the garment.

The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, headband, hat/cap, collar, wristband, stocking, sock, or shoe, athletic clothing, personal protection equipment, swimwear, wetsuit or drysuit. The garment may be constructed from a woven or a non-woven material.

The garment may be constructed from natural fibres, synthetic fibres, or a natural fibre blended with one or more other materials which can be natural or synthetic. The yarn may be cotton. The cotton may be blended with polyester and/or viscose and/or polyamide according to the particular application. Silk may also be used as the natural fibre. Cellulose, wool, hemp and jute are also natural fibres that may be used in the garment. Polyester, polycotton, nylon and viscose are synthetic fibres that may be used in the garment.

The garment may be a tight-fitting garment. Beneficially, a tight-fitting garment helps ensure that any sensors of the garment are held in contact with or in the proximity of a skin surface of the wearer. The garment may be a compression garment. The garment may be an athletic garment such as an elastomeric athletic garment.

The garment may be a shirt. The marker may be located on the collar, yoke, sleeve, gauntlet, cuff, body, pocket, plackett, or fastener of the shirt. The shirt may comprise a plurality of markers. The plurality of markers may be located at a plurality of different positions on the shirt. The plurality of different positions on the shirt may comprise one or more of the collar, yoke, sleeve, gauntlet, cuff, body, pocket, plackett, or fastener of the shirt The garment may be a T-shirt. The marker may be located on the neckline, sleeve, cuff, body or hem of the T-shirt. The T-shirt may comprise a plurality of markers. The plurality of markers may be located at a plurality of different positions on the T-shirt. The plurality of different positions on the shirt may comprise one or more of the neckline, sleeve, cuff, body or hem of the T-shirt.

The communication unit may be a mobile/cellular communicator operable to communicate the data wirelessly via one or more base stations. The communication unit may provide wireless communication capabilities for the garment and enables the garment to communicate via one or more wireless communication protocols such as used for communication over: a wireless wide area network (WWAN), a wireless metroarea network (WMAN), a wireless local area network (WLAN), a wireless personal area network (WPAN), Bluetooth® Low Energy, Bluetooth® Mesh, Bluetooth® 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communication units may be provided for communicating over a combination of different communication protocols.

According to a fourth aspect of the invention, there is provided a system comprising a garment of the third aspect of the invention and an apparatus according to the second aspect of the invention. The apparatus may comprise one or more electronic devices may be operable to perform the method of the first aspect of the invention. The one or more electronic devices may be operable to: obtain an image of the garment; process the image to generate a representation of the visual symbol; and transmit the representation of the visual symbol to a server so as to activate a sensor of the garment identified by the code string to record activity data.

According to a fifth aspect of the invention, there is provided a computer program comprising instructions which, when the program is executed by a computer, cause the computer to carry out the method of the first aspect of the invention.

According to a sixth aspect of the invention, there is provided a computer readable storage medium comprising instructions which, when executed by a computer, cause the computer to carry out the method of the first aspect of the invention.

There is also provided a method of manufacturing a garment according to the third aspect of the invention. The method comprises generating a code string using a random number generator; encoding the code string into a visual symbol; and incorporating the visual symbol onto the garment.

According to a seventh aspect of the invention, there is provided method performed by a system comprising a server and a user electronic device. The method comprises the user electronic device obtaining an image of a garment, wherein the garment comprises a visual symbol. The visual symbol comprises a code string identifying the garment that is encoded into the visual symbol. The method comprises processing the image to generate a representation of the visual symbol. The method comprises transmitting the representation of the visual symbol to the server. The method comprises the server receiving, from the user electronic device, the representation of a visual symbol. The method comprises establishing, based on the representation of the visual symbol, the identity of the garment. The method comprises transmitting, to the identified garment, an authorisation code to activate a sensor of the garment to record activity data. The transmitting may be performed by the server or the user electronic device. The server may transmit the authorisation code indirectly via the user electronic device. The visual symbol may be located on an outside surface of the garment.

The system may also comprise the garment.

BRIEF DESCRIPTION OF THE DRAWINGS

Examples of the present disclosure will now be described with reference to the accompanying drawings, in which.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

According to aspects of the present invention, a garment is provided having a marker located on an outside surface of the garment. The marker comprises a code string identifying the garment encoded into a visual symbol. In more detail, a code is generated for the garment using a random number generator. The code may in a code format with sufficient address space to enable a sufficient number of different codes to be generated. For example, the code format may be in the form of a 14-character hexadecimal number. Once the code is generated by the random number generator, a processor running an algorithm converts the code into a visual symbol which is printed or otherwise manufactured onto the garment. Encoding the code into a visual symbol is beneficial because the original code cannot be parsed from the visual symbol without access to the encoding algorithm. Moreover, the visual symbol is easily machine readable by providing image data of the visual symbol captured using a camera. As an added benefit the visual symbol is also useable as a fiducial marker for tracking the motion of the garment.

The garment further comprises a sensor or more typically a plurality of sensors. The activity data obtained by the sensors is transmitted by a communication unit of the garment to a server. The transmission may be performed over a high throughput wireless communication protocol such as 5G.

The garment may be worn by a first person referred to as the "wearer". A second person referred to as the "user" is in possession of a user electronic device such as a mobile phone. The second person may desire to see activity data for the wearer as recorded by the sensors of the garment. For example, the user may be a personal trainer that may desire to view metrics such as the wearer's heartrate, respiration levels and hydration levels. The user may also be a healthcare professional such as a physiotherapist or doctor.

In some examples, the "user" and the "wearer" refer to the same person. For example, the user electronic device may be a television apparatus with an integrated camera. The wearer of the garment may stand in front of the television apparatus and may be captured by the camera of the television apparatus. The television apparatus may then display the activity data so that the wearer may view their activity information.

Figure 1:
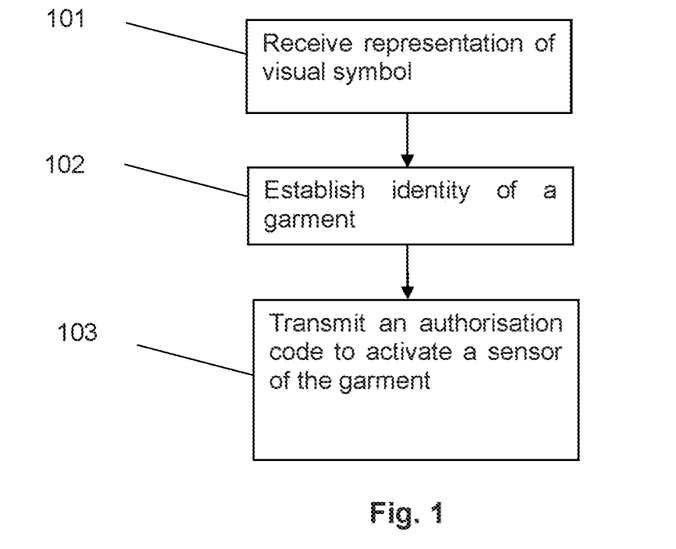
FIG. 1 shows a flow diagram for an example method according to aspects of the present invention.

Referring to FIG. 1, there is shown an example method according to the first aspect of the present invention that allows the user of to control a sensor of the garment to record activity data. The method is performed by a server in communication with a user electronic device. In some examples, the server and the user electronic device may be the same device.

In step 101 of the method, the server receives, from the user electronic device, a representation of a visual symbol located on an outside surface of a garment. The visual symbol comprises a code string identifying the garment that is encoded into the visual symbol. The representation of the visual symbol may be a data string. The visual symbol may be converted into the data string by the user electronic device performing an image processing operation. The user electronic device may generate the data string by simply digitising the image of the visual symbol. The digitised version of the visual symbol may then be transmitted to a server which decodes the symbol. Alternatively, the user electronic device may translate the visual symbol into an encrypted version of the code string. The encrypted version of the code string may be transmitted by a server for decoding. The user electronic device may decode the data string but it is generally beneficial to keep the decoding algorithm private.

In step 102 of the method, the server establishes, based on the representation of the visual symbol, the identity of the garment. In more detail, the server may decode the data string and compare the decoded data string to the original code string (which may be stored securely on the server) to determine whether the decoded data string matches the code string. The server may store code strings for a number of garments and therefore the decoded data string may be compared against a plurality of code strings stored in the database. If the decoded data string matches a code string in the database, the server may identify the garment associated with the code string and may generate an authorisation code for activating a sensor of the garment to record activity data. The activity data may be transmitted to the server, the user electronic device, or to another server that is communicatively coupled to the server.

In some examples, the plurality of code strings stored in the database may relate to garments with sensors that are authorised to record data. If a garment is stolen, for example, the owner may report the theft to the service provider. The service provider may then remove the code string associated with the garment from the database or flag the code string to identify that the garment has been stolen and is no longer authorised to record data. Then, when the server subsequently attempts to establish the identity of the garment, the authorisation process will fail and the authorisation code for activating the sensor of the garment will not be generated and transmitted to the garment. In this way, the sensor is not activated and the functionality of the garment is restricted.

In some examples, the authorisation code may only be generated if the garment is associated with a user that has paid for or has the required permission to use the sensor. The sensor may be a "premium" sensor that is only available with certain payment plans. The method enables the selective activation of these sensors such that different levels of activation of the garment may be provided depending on the services required by the end user. In some examples, the user electronic device may also obtain a user credentials for the user. The user credential may be in the form of a password or passcode or biometric data. Any form of biometric data may be used such as fingerprint data, ECG data, or iris data. The user electronic device transmits the data string and the user credential to the server. The server then identifies the garment from the data string and authenticates the user based on the user credential. In more detail, the server may store the code string associated with the identified garment and the user credential indicating whether the user is authorised to access the activity data. This information may be stored in a database along with code strings for other garments and user credentials for other users. In response to receiving the data string and the user credential, the server decodes the data string and compares the decoded data string to the code string or strings in the database.

If the decided data string matches a code string in the database, the server identifies the garment associated with the code string. The server then determines based on the received user credential whether the user is authenticated as having permission to access the activity data. Different users may have access to different sensors or types of biodata recorded by the sensors. That is, different users may have different permission levels in relation to controlling the sensors of the garment. For example, a personal trainer may be able to activate the sensors to record a limited amount of activity data for the garment. The personal trainer may be able, for example, to record heart rate, respiration rate, and hydration level data. The personal trainer may not be able to record other activity data which may relate to more personal information. In contrast, a healthcare professional may be able to record all of the data for the garment. The access level may be indicated by the user credential.

It will be appreciated that the step of obtaining user credentials is not required in all embodiments of the present invention. For example, if only trusted user electronic devices are able to communicate with the server then a separate step of authorising the user will not always be required.

In step 103 of the method, the server transmits an authorisation code to the garment to activate a sensor of the garment. The authorisation code may be received by a communication unit of the garment. The authorisation code may be transmitted via the user electronic device. That is, the user electronic device may receive the authorisation code from the server and transmit the same to the garment.

The server may receive the activity data recorded by the sensor and may transmit the activity data to the user electronic device. The user electronic device may directly receive activity data from the server. The activity data transmitted to the user electronic device may not be the same as the activity data recorded by the sensors. This is because the server may perform one or more processing operations on the received activity data.

Figure 2:
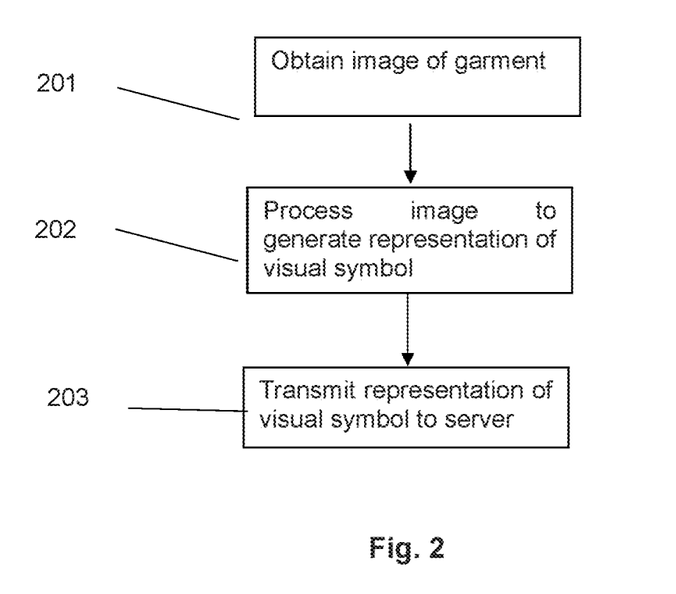
FIG. 2 shows a flow diagram for an example method according to aspects of the present invention.

Referring to FIG. 2, there is shown a method performed by a user electronic device in communication with a server.

In step 201 of the method, the user electronic device obtains an image of a garment. The garment comprises a visual symbol located on an outside surface of the garment.

The visual symbol comprises a code string identifying the garment that is encoded into the visual symbol.

In step 202 of the method, the user electronic device processes the image to generate a representation of the visual symbol.

In step 203 of the method, the user electronic device transmits the representation of the visual symbol to a server so as to activate a sensor of the garment identified by the code string to record activity data.

Figure 3A:
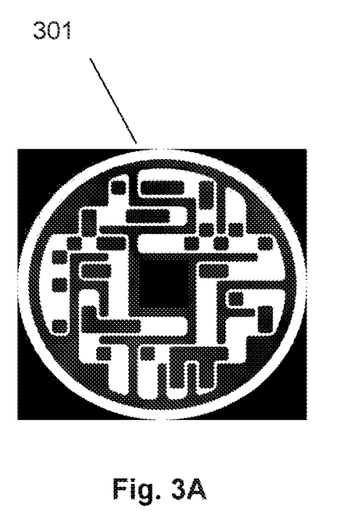
FIGS. 3A and 3B show example markers in accordance with aspects of the present invention.

Referring to FIG. 3A, there is shown an example marker 301 in accordance with the present invention. The marker 301 in this example is based on the Vcode® provided by VST Enterprises™ and comprises a visual symbol in the form of black marks upon white pathways. The black marks represent the characters in the code string. The visual symbol may additionally encode redundant information for error detection, correction, and uniqueness over different rotations of the marker.

Figure 3B:
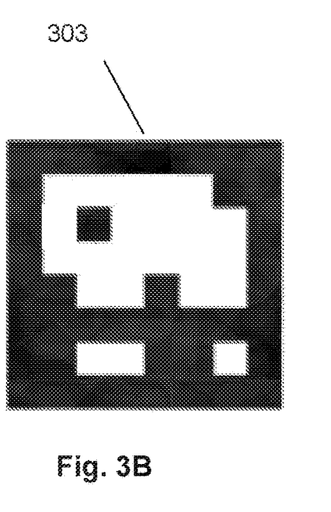

Referring to FIG. 3B, there is shown another example marker 303 in accordance with the present invention. The marker 303 in this example is derived from the AR marker system known as ARTag. The marker 303 comprises a visual symbol in the form of a 6×6 grid of black or white cells which represent 36 binary '0' or '1' symbols. The 36-bit sequence encodes the code string and may additionally encode redundant information for error detection, correction and uniqueness over the different rotations of the marker.

In both examples, the code string/data string may be retrieved from the marker 301, 303 by processing an image containing the visual symbol. It will be appreciated that known image processing operations such as contour extraction and edge detection will be used to read the symbol from the image.

It will be appreciated that the marker 301, 303 in accordance with the present invention is not limited to the examples of markers shown in FIGS. 3A and 3B. Instead, other forms of markers 301, 303 that encode a code string identifying the garment into a visual symbol may be used. In most preferred examples, the markers 301, 303 are additionally used as fiducial markers 301, 303. This means that the markers 301, 303 act as a point of reference for the garment and thus enable the position of the garment and the motion of the garment over time to be monitored simply by capturing images of the garment. Generally, the marker 301, 303 is preferred to be a bitonal marker as this means that there is no need to identify different shades of grey within the marker 301, 303 during the image processing operation to identify and decode the marker 301, 303. This beneficially helps reduce the sensitive to lighting conditions and camera settings. Of course, in some examples the marker 301, 303 may not be bitonal and may comprise different grey levels or indeed different colours.

Figure 4:
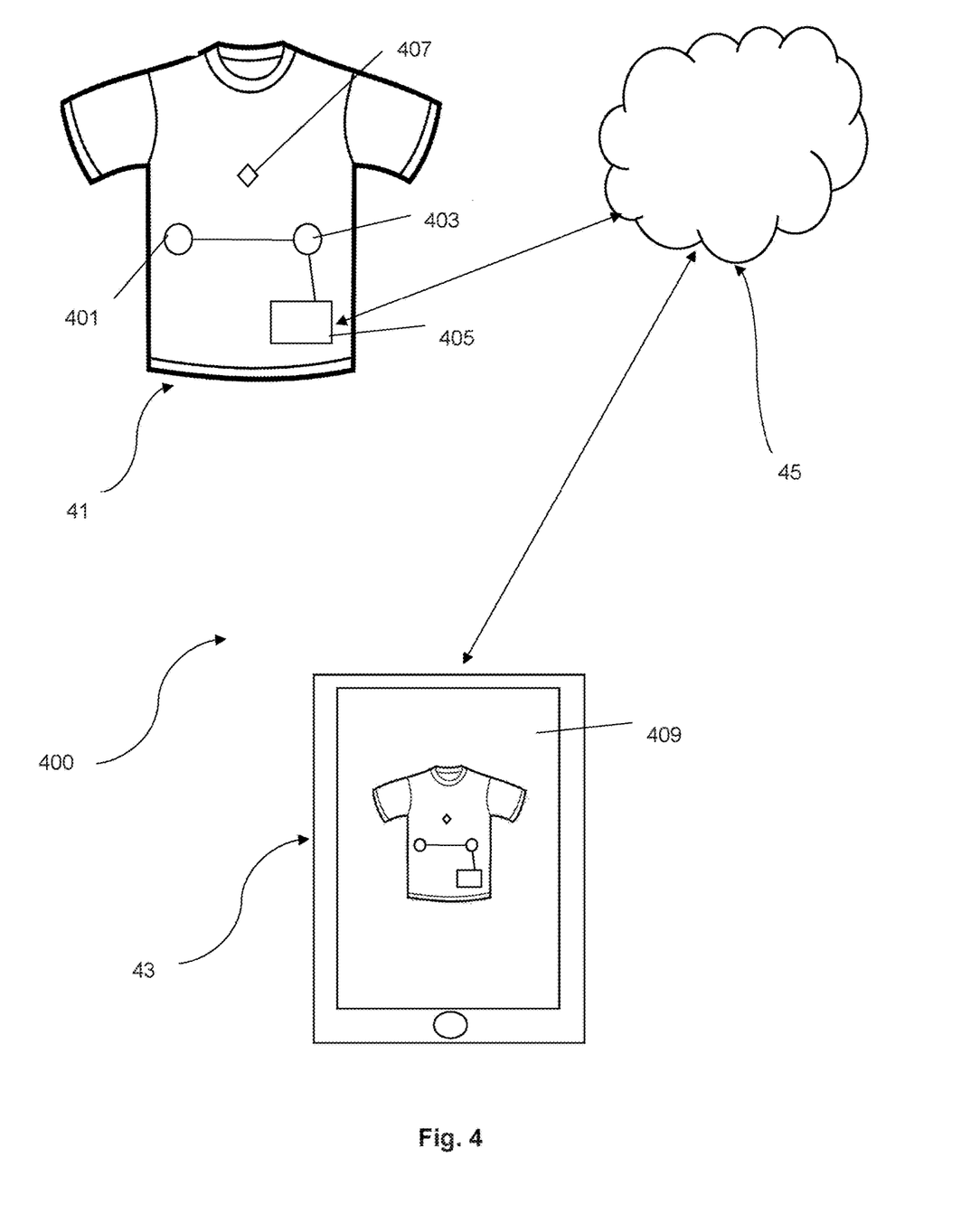
FIG. 4 shows an example system according to aspects of the present invention.

Referring to FIG. 4, there is shown an example garment 41, user electronic device 43, and server 45 in accordance with aspects of the present invention. The garment 41, user electronic device 43, and server 45 form an example system 400 in accordance with aspects of the invention.

The garment 41 in the example of FIG. 4 is in the form of a T-shirt. The garment 41 comprises two sensors 401, 403 arranged to monitor the activity of the wearer of the garment 41. In this example, one of the sensors 401 acts as a monitoring unit and the other sensor 403 acts as a reference unit. The sensors 401, 403 are communicatively coupled to a communication unit 405 arranged to communicate activity data to the server 45. The garment 41 comprises a marker 407 located on the outside surface of the garment 41 and in particular on the main body of the T-shirt. The marker 407 comprises a code string identifying the garment encoded into a visual symbol as shown in FIGS. 3A and 3B. The marker 407 is arranged such that, when imaged by an image capturing device such as the camera of the user electronic device 43, the marker 407 is useable to generate an authorisation code. The communication unit 405 is arranged to receive the activation code from the server 45/user electronic device 43. One or both of the sensors 401, 403 are arranged to be activated to record activity data according to the authorisation code received by the communication unit 405. Once the sensor 401, 403 is activated to record activity data, the communication unit 405 may receive the activity data from the sensor 401, 403 and transmit the same to the server 45/user electronic device 43.

The user electronic device 45 in the example of FIG. 4 is in the form of a mobile phone with an integrated camera. The user electronic device 43 comprises a communication unit, a storage, a controller, a display 409, a camera and a user input unit. The controller provides overall control to the user electronic device. The communication unit transmits and receives various pieces of information required for communication with a server under the control of the controller. The communication unit transmits the data string to the server and receives activity data from the server. The user input unit receives inputs from the user such as a user credential. The camera captured the image of the garment. The storage stores information for the user terminal. The display 409 is arranged to show a live view image of the scene captured by the camera. The display 409 may be a presence-sensitive display and therefore may comprise the user input unit. The presence-sensitive display may include a display component and a presence-sensitive input component. The presence sensitive display may be a touch-screen display arranged to provide the user interface.

The user electronic device 43 may also include a biometric sensor. The biometric sensor may be used to identify a user or users of device based on unique physiological features. The biometric sensor may be: a fingerprint sensor used to capture an image of a users fingerprint; an iris scanner or a retina scanner configured to capture an image of a users iris or retina; an ECG module used to measure the user's ECG; or the camera of the user electronic arranged to capture the face of the user. The biometric sensor may be an internal module of the user electronic device. The biometric module may be an external (stand-alone) device which may be coupled to the user electronic device by a wired or wireless link.

User electronic devices in accordance with the present invention are not limited to mobile phones and may take the form of any electronic device which may be used by a user to perform the methods according to aspects of the present invention. The user electronic device may be a mobile electronic device such as a smartphone, tablet personal computer (PC), mobile phone, smart phone, video telephone, laptop PC, netbook computer, personal digital assistant (PDA), mobile medical device, camera or wearable device. The wearable device may include a head-mounted device such as an Augmented Reality, Virtual Reality or Mixed Reality head-mounted device. The user electronic device may be desktop PC, workstations, television apparatus or a projector, e.g. arranged to project a display onto a surface.

The server 45 may be a single device or may comprise a plurality of distributed devices communicatively coupled to one another, e.g. as a cloud-based server such as cloud server network. The server comprises a communication unit, a storage, and a controller. The controller provides overall control to the server. The communication unit transmits and receives various pieces of information required for communication with a user electronic device and/or garment under the control of the controller. The storage stores information for the server such as code strings identifying garments and user credential information.

Figure 5:
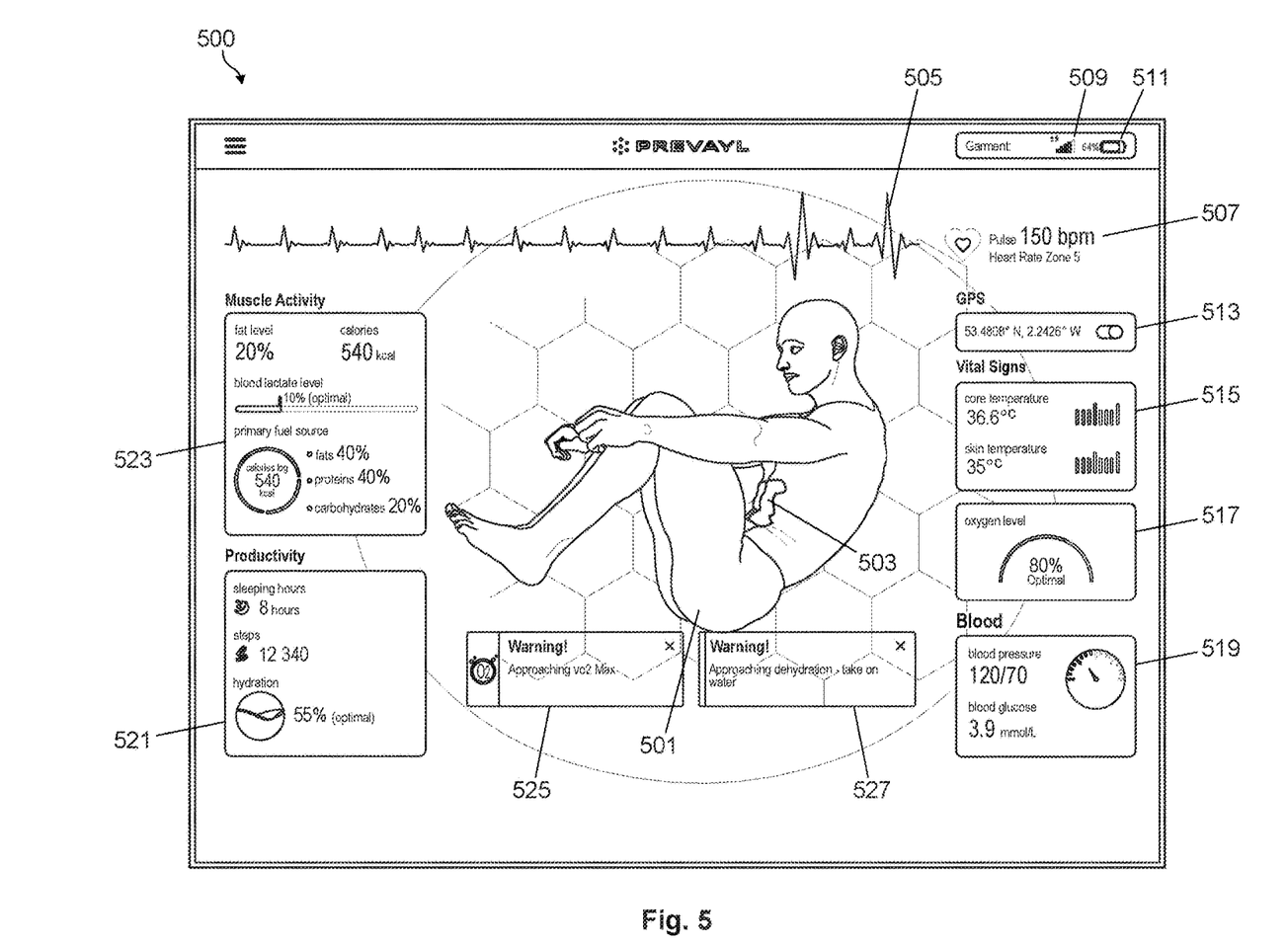
FIG. 5 shows an example user interface according to aspects of the present invention.

Referring to FIG. 5, there is shown an example user interface 500 displayed on the user electronic device 43.

The user interface includes a display of a representation of the wearer of the garment 501. In this example, the representation of the wearer of the garment 501 is in the form of a 3D avatar. The 3D avatar will move as the wearer moves as a result of the motion tracking performed using the fiducial markers provided on the garment 41. A more refined motion estimate may be provided by incorporating additional active motion sensors such as accelerometers and gyroscopes into the garment. In other examples, the displayed representation of the wearer of the garment 41 is in the form of a live view image as captured by the camera of the user electronic device 43. In this example, the additional active motion sensors are not required for the garment 41 but may still be provided.

The user interface 500 also includes representation of the activity data 503 received from the server 45. The representation of the activity data 503 in this example is the form of an object 503 that overlays the abdominal muscles of the wearer. The representation of the activity data 503 changes colour depending on whether the activity data indicates that the abdominal muscles are in contraction or relaxation. In FIG. 5, the abdominal muscles are in contraction and as such the object 503 has a dark colour. When the abdominal muscles are in relaxation the colour of the object 503 lightens. Of course, other visual representations of the activity data relating to the abdominal muscles may be provided.

The object 503 is displayed at a position determined according to the location of the marker on the garment 41. In particular, the marker is a fiducial marker that acts as a reference position for the garment 41 in relation to the wearer of the garment 41. The position of the object to be displayed is determined using the position of the marker (x1, y1) in the image and a predetermined displacement (x2, y2) from the marker to a feature of interest on the wearer such as the abdominal muscles. In particular, the position of the object 503 to be displayed can be determined as (x1, y1)+(x2, y2).

The user interface 500 of FIG. 5 displays additional activity data for the wearer and other data for the garment 41 at positions which are not determined based on the location of the marker on the garment 41. The user interface 500 includes an ECG trace 505 and heartrate data 507; the signal strength 509 for the communication unit of the garment 41; the battery level 511 for a battery of the garment 41; GPS coordinate data 513; core body temperature and skin surface temperature 515; the oxygen level 517, blood pressure and blood glucose levels 519, sleep tracking, step tracking and hydration level 521, and fat level, calories burned, blood lactate level as well as an indication of the type of calories burned 523. The user interface 500 also displays warnings 525, 527 indicating the wearer's VO2 and hydration levels are concerning. Of course, the user interface 500 in FIG. 5 is just one example interface and other forms of bio data may be displayed to the user in a different way.

Figure 6:
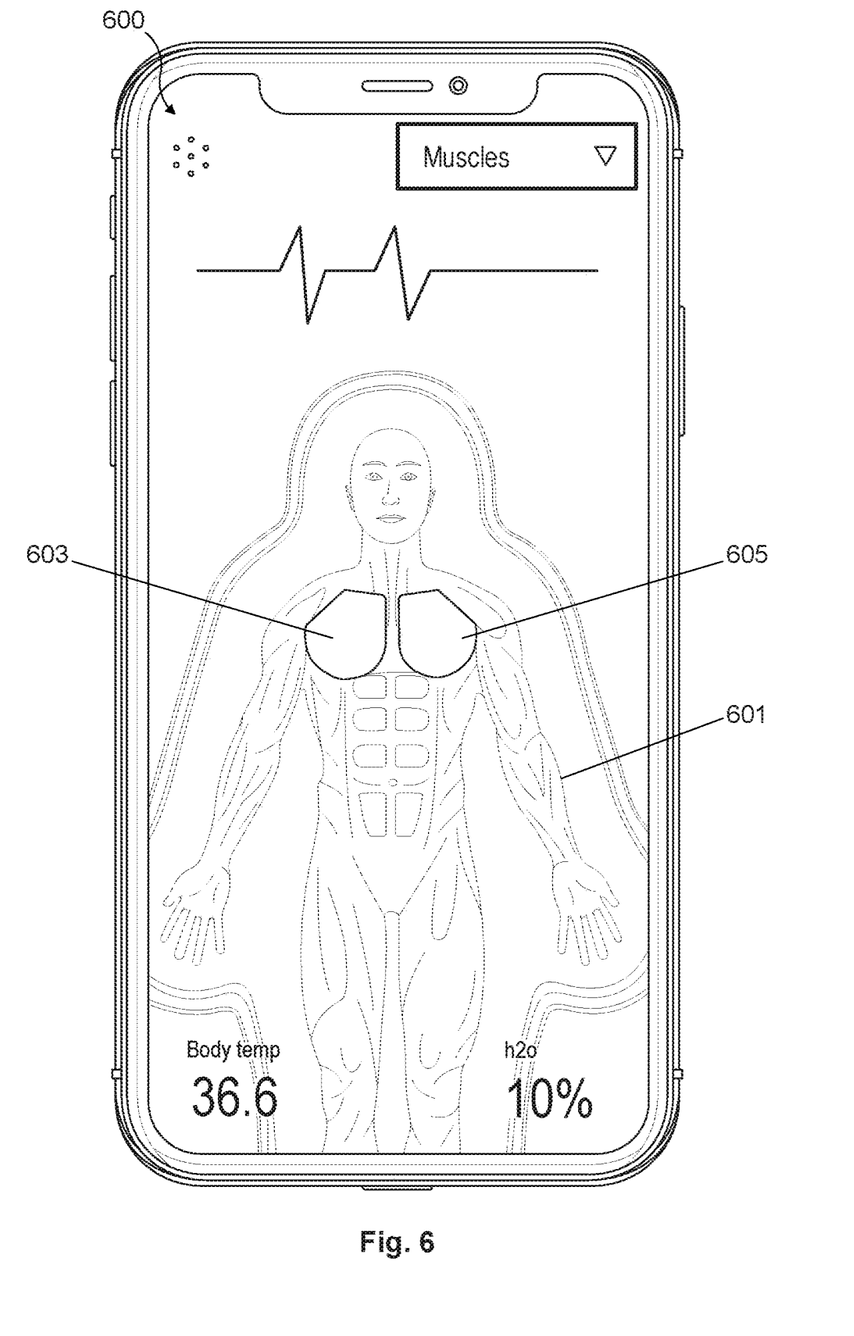
FIG. 6 shows an example user interface according to aspects of the present invention.

Referring to FIG. 6, there is shown another example user interface 600 displayed on the user electronic device 43. The user interface 600 displays a representation of the wearer 601 which may be a 3D avatar or a live view image of the wearer. In addition, the user interface 600 overlays the representation of the wearer 601 with two objects 603, 605. The two objects 603, 605 are displayed at positions that correspond to the location of the pectoral muscle area of the wearer. The position of the objects 603, 605 are determined according to the location of the marker on the garment as described above in relation to FIG. 6. The objects 603, 605 are representations of the activity data of the wearer relating to the pectoral muscle area. The objects 603, 605 change colour based on the received activity data for example to indicate whether the muscles are in contraction or relaxation.

Figure 7:
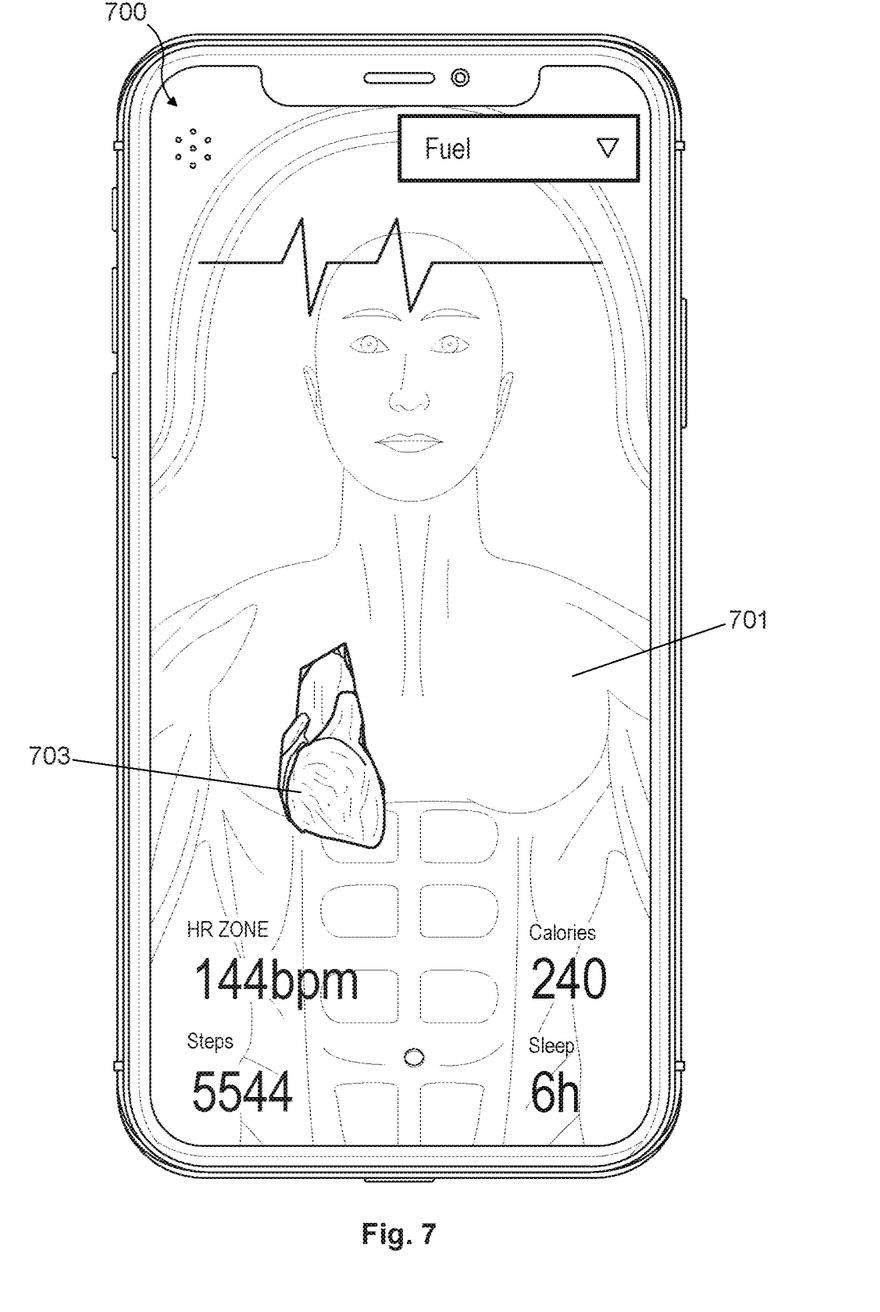
FIG. 7 shows an example user interface according to aspects of the present invention.

Referring to FIG. 7, there is shown another example user interface 700 displayed on the user electronic device 43. The user interface 700 displays a representation of the wearer 701 which may be a 3D avatar or a live view image of the wearer. In addition, the user interface 700 overlays the representation of the wearer 701 with an object 703. The object 703 is displayed at a position that corresponds to the location of the heart (the representation of the wearer 701 is displayed as a mirror image in FIG. 7). The position of the object 703 is determined according to the location of the marker on the garment as described above in relation to FIG. 5. The object 703 is a representation of the cardiac activity data of the wearer. The object 703 is in particular an animated 3D model of a heart that beats at a rate corresponding to the heart rate of the wearer as determined from the activity data.

In addition, the user interface may display information relating to past or predicted future movements undertaken by the wearer. The garment may incorporate one or more motion sensors such as accelerometers or gyroscopes which may be used to derive position and velocity data for the wearer. This information may be displayed such that the user can view how the wearer has moved over time. Moreover, based on past motion information a future motion of the user may be estimated and displayed. The motion information may be displayed as a series of points on the display such as in the form of a point cloud.

Figure 8:
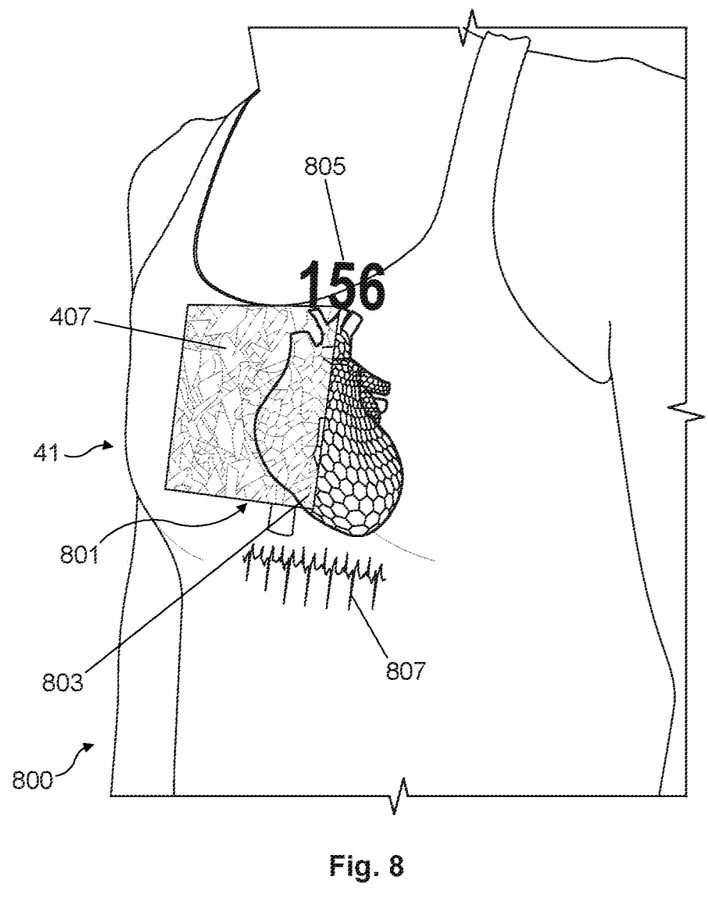
FIG. 8 shows an example user interface according to aspects of the present invention.

Referring to FIG. 8, there is shown an example user interface according to aspects of the present invention. The user interface displays a live view image 800 that is captured by a camera communicatively coupled to the electronic device. The live view image 800 is a live video feed of the wearer wearing the garment 41. The garment 41 has a fiducial marker 407 located on an outside surface of the garment. The live view image 800 is processed to determine the location of the fiducial marker 407. The display of the live view image 800 is augmented with the display of an augmented reality object 801. The position of the augmented reality object 801 on the display is determined based on the determined location of the fiducial marker 407. That is, the augmented reality object 801 is always displayed at a predetermined displacement from the fiducial marker 407. The effect of this is that the augmented reality object 801 always appears on the display to overlay the cardiac region of the wearer of the garment 41. The augmented reality object 801 provides a representation of the cardiac activity data which is recorded by one or more sensors (not visible) of the garment. The augmented reality object 801 comprises a 3D model of the heart 803 that is animated to beat at a rate corresponding to the heart rate of the wearer as recorded by the sensor(s) of the garment 41. The 3D model of the heart 803 changes colour based on the heart rate of the wearer. The 3D model of the heart 803 is green when the heart rate is at a low value (e.g. less than 100 beats per minute), yellow when the heart rate is at a medium value (e.g. between 100 and 145 beats per minute) and red when the heart rate is at a high value (e.g. greater than 145 beats per minute). Of course, other colours may be used. The 3D model of the heart may additionally or separately change size, shape or texture depending on the heart rate. The augmented reality object 801 comprises a numerical display of the heart rate 805. The augmented reality object 801 comprises a display of ECG data 807 for the wearer. The display of the heart rate 805 and the ECG data 807 may also change colour, size, shape or texture depending on the heart rate. Conveniently, the present invention conveys cardiac information to the observer in a way that is easy and intuitive to understand as the augmented reality object 801 is always positioned to overlay the cardiac region of the wearer.

In summary, there is provided a method of controlling a garment to record activity data. The method comprises receiving a representation of a visual symbol, wherein the visual symbol comprises a code string identifying the garment that is encoded into the visual symbol 101. The method comprises establishing, based on the representation of the visual symbol, the identity of the garment 102. The method comprises transmitting, to the identified garment, an authorisation code to activate a sensor of the garment to record activity data 103.

While the particular examples mentioned above refer to wearable articles in the form of garments, it will be appreciated that the present disclosure is not limited to such examples and other forms of wearable article are within the scope of the present disclosure. The wearable article may be, for example, any form of electronic device which may be worn by a user such as a smart watch, necklace, bracelet, or glasses. The wearable article may be a textile article.

While the particular examples mentioned above refer to visual symbols located on an outside surface of a garment or other form of wearable article, it will be appreciated that the present disclosure is not limited to such examples. Other forms of visual symbol such as those which are readable from the outside of the garment but not necessarily provided on the outside surface of the garment are within the scope of the present disclosure.

While the particular examples mentioned above refer to methods performed by a server and user electronic device, it be appreciated that the present disclosure is not limited to such examples. All of the steps of the methods described herein may be performed by an electronic device such as a user electronic device without, necessarily, requiring communication with a server. All of the steps of the methods described herein may be performed by a server without, necessarily, requiring communication with a user electronic device.

In some examples according to the present disclosure, electronics components of the garment such as the communication unit and sensor are removable from the garment. The electronics components may be removably contained within a pocket of the garment.

The following examples are described to facilitate understanding of the invention:

1. A method performed by a server, the method comprising:
   receiving, from a user electronic device, a representation of a visual symbol located on an outside surface of a garment, wherein the visual symbol comprises a code string identifying the garment that is encoded into the visual symbol;
   establishing, based on the representation of the visual symbol, the identity of the garment;
   transmitting, to the identified garment, an authorisation code to activate a sensor of the garment to record activity data.
2. The method of example 1, wherein the representation of the visual symbol is a data string representing the visual symbol.
3. The method of example 1 or example 2, wherein establishing, based on the data string, the identity of the garment comprises decoding the data string so as to obtain the code string and further comprises identifying the garment based on the code string.
4. The method of any of examples 1 to 3, further comprising:
   receiving, from the user electronic device, a user credential;
   establishing, based on the user credential, whether the user is authorised to activate the sensor; and
   transmitting the authorisation code to the identified garment only if the user is authorised to activate the sensor.
5. The method of any of examples 1 to 4, further comprising:
   receiving the recorded activity data from the garment; and
   transmitting the activity data to the user electronic device.
6. The method performed by a user electronic device, the method comprising:
   obtaining an image of a garment, wherein the garment comprises a visual symbol located on an outside surface of the garment, wherein the visual symbol comprises a code string identifying the garment that is encoded into the visual symbol;
   processing the image to generate a representation of the visual symbol; and transmitting the representation of the visual symbol to a server so as to activate a sensor of the garment identified by the code string to record activity data.
7. The method of example 6, wherein the representation of the visual symbol is a data string representing the visual symbol.
8. The method of example 6 or example 7, further comprising obtaining a user credential from a user, wherein the sensor is only activated to record activity data if the user is authorised, based on the obtained user credential, as having permission to access the activity data.
9. The method of example 8, further comprising transmitting the user credential to a server so that the server is able to determine if the user is authorised as having permission to activate the sensor based on the obtained user credential.
10. The method of any of examples 6 to 9, further comprising receiving activity data from the server.
11. The method of any of examples 6 to 11, wherein the visual symbol is part of a fiducial marker located on the outside surface of the garment, and wherein the method further comprises processing the image to determine the location of the fiducial marker.
12. The method of example 11, further comprising displaying a representation of the received activity data on a display.
13. The method of example 12, wherein the position of the representation of the activity data on the display is determined according to the determined location of the fiducial marker.

14. The method of example 12 or 13, further comprising simultaneously displaying a representation of a wearer of the garment with the representation of the activity data on the display.
15. The method of example 14, wherein the representation of the activity data at least partially overlays the displayed representation of the wearer.
16. The method of example 14 or 15, wherein displaying the representation of the wearer of the garment comprises displaying the obtained image.
17. The method of example 14 or 15, wherein displaying the representation of the wearer of the garment comprises displaying an avatar representation of the wearer, optionally wherein the avatar representation of the wearer is a 3D representation of the wearer.
18. The method of any of examples 14 to 17, wherein the representation of the activity data is in the form of an augmented reality object.
19. A garment comprising:
a sensor arranged to monitor the activity of the wearer of the garment;
a communication unit arranged to receive activity data for the wearer from the sensor and transmit the activity data to an external device; and
at least one marker located on an outside surface of the garment, the at least one marker comprising a code string identifying the garment encoded into a visual symbol and arranged such that, when imaged by an image capturing device, the at least one marker is useable to control a sensor of the garment identified by the code string to record activity data.
20. A method of manufacturing a garment of example 19, the method comprising:
generating a code string using a random number generator;
encoding the code string into a visual symbol; and
incorporating the visual symbol onto the garment.
21. A system comprising a garment of example 19; and one or more electronic devices operable to:
obtain an image of the garment; process the image to generate a representation of the visual symbol; and
transmit the representation of the visual symbol to a server so as to activate a sensor of the garment identified by the code string to record activity data.
22. A computer program comprising instructions which, when the program is executed by a computer, cause the computer to carry out the method of any of examples 1 to 18.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive. Throughout this specification, the term "comprising" or "comprises" means including the component(s) specified but not to the exclusion of the presence of others.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:
1. A method performed by a user electronic device, the method comprising:
obtaining an image of a garment, wherein the garment comprises a visual symbol located on an outside surface of the garment, wherein the visual symbol comprises a code string identifying the garment that is encoded into the visual symbol;
processing the image to generate a representation of the visual symbol;
transmitting the representation of the visual symbol to a server so as to activate a sensor of the garment identified by the code string to record activity data;
obtaining a user credential from a user, wherein the sensor is only activated to record activity data if the user is authorised, based on the obtained user credential, as having permission to access the activity data; and
transmitting the user credential to a server so that the server is able to determine if the user is authorised as having permission to activate the sensor based on the obtained user credential.
2. The method of claim 1, wherein the representation of the visual symbol is a data string representing the visual symbol.
3. The method of claim 1, further comprising receiving activity data from the server.
4. The method of claim 3, wherein the visual symbol is part of a fiducial marker located on the outside surface of the garment, and wherein the method further comprises processing the image to determine the location of the fiducial marker.

5. The method of claim 4, further comprising displaying a representation of the received activity data on a display.

6. The method of claim 5, wherein the position of the representation of the activity data on the display is determined according to the determined location of the fiducial marker.

7. The method of claim 5, further comprising simultaneously displaying a representation of a wearer of the garment with the representation of the activity data on the display.

8. The method of claim 7, wherein the representation of the activity data at least partially overlays the displayed representation of the wearer.

* * * * *